(12) United States Patent
Fischer

(10) Patent No.: US 7,387,993 B2
(45) Date of Patent: Jun. 17, 2008

(54) MANNAN-BINDING LECTIN (MBL) TREATMENT OF INFECTIONS IN INDIVIDUALS TREATED WITH TNF-αINHIBITORS

(75) Inventor: Per Fischer, Allerød (DK)

(73) Assignee: Natimmune A/S, Copenhagen (DK)

( * ) Notice: Subject to any disclaimer, the term of this patent is extended or adjusted under 35 U.S.C. 154(b) by 0 days.

(21) Appl. No.: 10/332,712

(22) PCT Filed: Jul. 13, 2001

(86) PCT No.: PCT/DK01/00491

§ 371 (c)(1),
(2), (4) Date: Jun. 30, 2003

(87) PCT Pub. No.: WO02/05833

PCT Pub. Date: Jan. 24, 2002

(65) Prior Publication Data

US 2004/0029785 A1 Feb. 12, 2004

(30) Foreign Application Priority Data

Jul. 13, 2000 (DK) .............................. 2000 01088

(51) Int. Cl.
*A61K 38/00* (2006.01)
(52) U.S. Cl. ......................................................... 514/2
(58) Field of Classification Search ..................... 514/8, 514/2, 12, 54; 530/350; 435/69.1, 320.1, 435/252.1, 254.1, 254.4, 7.1; 424/134.1
See application file for complete search history.

(56) References Cited

U.S. PATENT DOCUMENTS 6,562,784 B1 * 5/2003 Thiel et al. ..................... 514/8

OTHER PUBLICATIONS

Hamilton et al., Tumour necrosis factor-alpha blockade: a new era for effective management of rheumatoid arthritis, Expert Opin Pharmacother. Jul. 2000;1(5):1041-52.*
Bala et al., Inhibition of Tumor Necrosis Factor Alpha Alters Resistance to Mycobacterium avium Complex Infection in Mice, Antimicrobial Agents and Chemotherapy, Sep. 1998, , vol. 42, No. 9, pp. 2336-2341.*
Weis WI, Taylor ME and Drickamer K (1998) The C-type lectin superfamily in the immune system. *Immunological Reviews* 163: 19-34.
Holmskov, U., Malhotra, R., Sim, R.B., and Jensenius, J.C. (Feb. 1994) Collectins: collagenous C-type lectins of the innate immune defense system. *Immunol.Today* 15:67-74.

Turner, M.W. (Nov. 1996) Mannose-binding lectin: the pluripotent molecule of the innate immune system. *Immunol.Today* 17:532-540.
Janeway CA, Travers P, Walport M and Capra JD (1999) Immunobiology, the immune system in health and disease, Fourth Edition, Churchill Livingstone).
Matsushita, M. and Fujita, T (Dec. 1992). Activation of the classical complement pathway by mannose-binding protein in association with a novel C1s-like serine protease. *J.Exp.Med.* 176:1497-1502.
Thiel S, Vorup-Jensen T, Stover CM, Schwaeble W, Laursen SB, Poulsen K, Willis AC, Eggleton P, Hansen S, Holmskov U, Reid KB and Jensenius JC (Apr. 1997) A second serine protease associated with mannan-binding lectin that activates complement. *Nature*, 386(6624): 506-510.
Stover CM, Thiel S, Thelen M, Lynch NJ, Vorup-Jensen T, Jensenius JC and Schwaeble WJ (1999) Two constituents of the initiation complex of the mannan-binding lectin activation pathway of complement are encoded by a single structure gene. *J Immunol* 162: 3481-3490.
Thiel S, Holmskov U, Hviid L, Laursen SB and Jensenius JC (1992) The concentration of the C-type lectin, mannan-binding protein, in human plasma increases during an acute phase response. *Clin Exp Immunol* 90: 31-35.
Madsen, H.O., Garred, P., Kurtzhals, J.A., Lamm, L.U., Ryder, L.P., Thiel, S., and Svejgaard, A. (1994) A new frequent allele is the missing link in the structural polymorphism of the human mannan-binding protein. *Immunogenetics* 40:37-44.
Summerfield JA, Ryder S, Sumiya M, Thursz M, Gorchein A, Monteil MA and Turner MW (Apr. 8, 1995) Mannose binding protein gene mutations associated with unusual and severe infections in adults. *Lancet* 345: 886-889.
Garred P, Madsen HO, Hofmann B and Svejgaard A (Oct. 7, 1995) Increased frequency of homozygosity of abnormal mannan binding protein alleles in patients with suspected immunodeficiency. *Lancet* 346: 941-943.
Summerfield JA, Sumiya M, Levin M and Turner MW (Apr. 26, 1997) Association of mutations in mannose-binding protein gene with childhood infection in consecutive hospital series. *BioMed J* 314: 1229-1232.
van Emmerik, LC, Kuijper, EJ, Fijen, Cap, Dankert, J, and Thiel, S (1994) Binding of mannan-binding protein to various bacterial pathogens of meningitis. *Clin.Exp.Immunol.* 97:411-416.

(Continued)

*Primary Examiner*—Robert B. Mondesi
(74) *Attorney, Agent, or Firm*—Iver P. Cooper

(57) ABSTRACT

The present invention relates to the use of subunits and oligomers of mannan-binding lectin (MBL) in prophylactic and/or curative treatment of infections in an individual receiving TNF-inhibiting treatment, in particular TNF-α-inhibiting treatment. The MBL may be administered together with an antimicrobial agent, for example as a kit-of-parts.

52 Claims, No Drawings

OTHER PUBLICATIONS

Jack DL, Dodds AW, Anwar N, Ison CA, Law A, Frosch M, Turner MW and Klein NJ (1998) Activation of complement by Mannose-binding lectin on isogenic mutants of *Neisseria meningitidis* seroproup B. *J Immunol* 160: 1346-1353.

Miller, M.E., Seals, J., Kaye, R., and Levitsky, L.C. (Jul. 13, 1968) A familial, plasma-associated defect of phagocytosis. A new cause of recurrent bacterial infections. *The.Lancet* :60-63.

Super, M., Thiel, S., Lu, J., Levinsky, R.J., and Turner, M.W. (Nov. 25, 1989) Association of low levels of mannan-binding protein with a common defect of opsonisation. *Lancet* 2:1236-1239.

Nielsen, S.L., Andersen, P.L., Koch, C., Jensenius, J.C., and Thiel, S. (1995) The level of the serum opsonin, mannan-binding protein in HIV-1 antibody-positive patients. *Clin. Exp. Immunol.* 100:219-222.

Christiansen, O.B., Kilpatrick, D.C., Souter, V., Varming, K., Thiel, S., Jensenius,J.C. (1999) Mannan-binding lectin deficiency is associated with unexplained recurrent miscarriage. *Scand. J. Immunol.*, 49, 193-196.

Garred, P, Harboe, M, Oettinger, T, Koch, C, and Svejgaard, A (1994) Dual role of mannan-binding protein in infections: Another case of heterosis ? *Eur.J.Immunogen.* 21:125-131.

Hoal-Van Helden EG, Epstein J, Victor TC, Hon D, Lewis LA, Beyers N, Zurakowski D, Ezekowitz AB, Van Helden PD (1999) Mannose-binding protein B allele confers protection against tuberculous meningitis. *Pediatr Res* 45:459-64.

Fischer, PB, Ellerman-Eriksen, S, Thiel, S, Jensenius, JC, and Mogensen, SC (1994) Mannan-binding protein and bovine conglutinin mediate enhancement of herpes simplex virus type-2 infection in mice. *Scand J Immunol* 39:439-445.

Valdimarsson H, Stefansson M, Vikingsdottir T, Arason GJ, Koch C, Thiel S and Jensenius JC (1998) Reconstitution of opsonizing activity by infusion of mannan-binding lectin (MBL) to MBL-deficient humans, Scand. J. Immunol. 48, 116-123.

Pizzo, PA (1993), Management of fever in patients with cancer and treatment-induced neutropenia, N Eng J Med, 328, 1323-1332.

Aittoniemi, J., Miettinen, A., Laine, S., Sinisalo, M., Laippala, P., Vilpo, L, Vilpo, J. (1999), Opsonising immunoglobulins and mannan-binding lectin in chronic lymphocytic leukemia, Leuk Lymphoma vol. 34(3-4):381-385.

Lehrnbecher T, Venzon D, de Haas M, Chanock SJ, Kuhl J. (1999) Assessment of measuring circulating levels of interleukin-6, interleukin-8, C-reactive protein, soluble Fc gamma receptor type III, and mannose-binding protein in febrile children with cancer and neutropenia. Clin Infect Dis, 29(2):414-419.

Lu, J., Thiel, S., Wiedemann, H., Timpl, R. & K.B.M. Reid (1990) Binding of the pentamer/hexamer forms of mannan-binding protein to zymosan activates the proenzyme $C1r_2C1s_2$ complex, of the classical pathway of complement without involvement of C1q. *J. Immunol.* 144:2287-2294.

Sastry, K., Herman, G.A., Day, L., Deignan, E., Bruns, G., Morton, C.C. & R.A.B. Ezekowitz (Oct. 1989) Exon Structure Reveals its Evolutionary Relationship to a Human Pulmonary Surfactant Gene and Localization to Chromosome 10. *J. Exp. Med.* 170:1175-1189.

Lipscombe, R.J., Sumiya, M., Summerfield, J.A. & M.W. Turner (1995) Distinct physicochemical characteristics of human mannose-binding protein expressed by individuals of differing genotype. *Immunology* 85:660-667.

WO 00/69894 (Steffen Thiel), Nov. 23, 2000, WIPO.

WO 92/16221 (Synergen), Oct. 1, 2992, WIPO.

WO 99/36507 (Genitrix), Jul. 22, 1999, WIPO.

WO 99/64453 (Statens Serum Institut), Dec. 16, 1999, WIPO.

* cited by examiner

MANNAN-BINDING LECTIN (MBL) TREATMENT OF INFECTIONS IN INDIVIDUALS TREATED WITH TNF-αINHIBITORS

The present invention pertains to the use of subunits and oligomers of mannan-binding lectin (MBL) in prophylactic and/or curative treatment of infections in an individual receiving TNF-inhibiting treatment.

Tumor Necrosis Factor: Monocytes and macrophages secrete cytokines known as tumor necrosis factor-α (TNF-α) and tumor necrosis factor-.beta. (TNF.beta.) in response to endotoxin or other stimuli. TNF-α is a soluble homotrimer of 17 kD protein subunits (Smith, et al., J. Biol. Chem. 262:6951-6954 (1987)). A membrane-bound 26 kD precursor form of TNF also exists (Kriegler, et al., Cell 53:45-53 (1988)). For reviews of TNF, see Beutler, et al., Nature 320:584 (1986), Old, Science 230:630 (1986), and Le, et al., Lab. Invest. 56:234 (1987).

Cells other than monocytes or macrophages also make TNF-α. For example, human non-monocytic tumor cell lines produce TNF (Rubin, et al., J. Exp. Med. 164:1350 (1986); Spriggs, et al., Proc. Natl. Acad. Sci. USA 84:6563 (1987)). $CD4^+$ and $CD8^+$ peripheral blood T lymphocytes and some cultured T and B cell lines (Cuturi, et al., J. Exp. Med. 165:1581 (1987); Sung, et al., J. Exp. Med. 168:1539 (1988)) also produce TNF-α.

TNF causes pro-inflammatory actions which result in tissue injury, such as inducing procoagulant activity on vascular endothelial cells (Pober, et al., J. Immunol. 136: 1680 (1986)), increasing the adherence of neutrophils and lymphocytes (Pober, et al., J. Immunol. 138:3319 (1987)), and stimulating the release of platelet activating factor from macrophages, neutrophils and vascular endothelial cells (Camussi, et al., J. Exp. Med. 166:1390 (1987)).

Recent evidence associates TNF with infections (Cerami, et al., Immunol. Today 9:28 (1988)), immune disorders, neoplastic pathologies (Oliff, et al., Cell 50:555 (1987)), autoimmune pathologies and graft-versus host pathologies (Piguet, et al., J. Exp. Med. 166:1280 (1987)). The association of TNF with cancer and infectious pathologies is often related to the host's catabolic state. Cancer patients suffer from weight loss, usually associated with anorexia.

The extensive wasting which is associated with cancer, and other diseases, is known as "cachexia" (Kern, et al. (J. Parent. Enter. Nutr. 12:286-298 (1988)). Cachexia includes progressive weight loss, anorexia, and persistent erosion of body mass in response to a malignant growth. The fundamental physiological derangement can relate to a decline in food intake relative to energy expenditure. The cachectic state causes most cancer morbidity and mortality. TNF can mediate cachexia in cancer, infectious pathology, and other catabolic states.

TNF also plays a central role in gram-negative sepsis and endotoxic shock (Michie, et al., Br. J. Surg. 76:670-671 (1989); Debets, et al., Second Vienna Shock Forum, p. 463-466 (1989); Simpson, et al., Crit. Care Clin. 5:27-47 (1989)), including fever, malaise, anorexia, and cachexia. Endotoxin strongly activates monocyte/macrophage production and secretion of TNF and other cytokines (Kornbluth, et al., J. Immunol. 137:2585-2591 (1986)). TNF and other monocyte-derived cytokines mediate the metabolic and neurohormonal responses to endotoxin (Michie, et al., New. Engl. J. Med. 318:1481-1486 (1988)). Endotoxin administration to human volunteers produces acute illness with flu-like symptoms including fever, tachycardia, increased metabolic rate and stress hormone release (Revhaug, et al., Arch. Surg. 123:162-170 (1988)). Circulating TNF increases in patients suffering from Gram-negative sepsis (Waage, et al., Lancet 1:355-357 (1987); Hammerle, et al., Second Vienna Shock Forum p. 715-718 (1989); Debets, et al., Crit. Care Med. 17:489-497 (1989); Calandra, et al., J. Infect. Dis. 161:982-987 (1990)).

The numerous biological effects of TNF-α and the closely related cytokine, TNF.beta. (lymphotoxin), are mediated by two TNF transmembrane receptors, both of which have been cloned. The p55 receptor (also termed TNF-R55, TNF-RI, or TNFR.beta.) is a 55 kd glycoprotein shown to transduce signals resulting in cytotoxic, anti-viral, and proliferative activities of TNF-α.

The p75 receptor (also termed TNF-R75, TNF-RII, or TNFRα) is a 75 kDa glycoprotein that has also been shown to transduce cytotoxic and proliferative signals as well as signals resulting in the secretion of GM-CSF. The extracellular domains of the two receptors have 28% homology and have in common a set of four subdomains defined by numerous conserved cysteine residues. The p75 receptor differs, however, by having a region adjacent to the transmembrane domain that is rich in proline residues and contains sites for O-linked glycosylation. Interestingly, the cytoplasmic domains of the two receptors share no apparent homology which is consistent with observations that they can transduce different signals to the interior of the cell.

TNF-α inhibiting proteins have been detected in normal human urine and in serum of patients with cancer or endotoxemia. These have since been shown to be the extracellular domains of TNF receptors derived by proteolytic cleavage of the transmembrane forms. Many of the same stimuli that result in TNF-α release also result in the release of the soluble receptors, suggesting that these soluble TNF-α inhibitors can serve as part of a negative feedback mechanism to control TNF-α activity.

Aderka, et al., Isrl. J. Med. Sci. 28:126-130 (1992) discloses soluble forms of TNF receptors (sTNF-Rs) which specifically bind TNF and thus can compete with cell surface TNF receptors to bind TNF (Seckinger, et al., J. Exp. Med. 167:1511-1516 (1988); Engelmann, et al., J. Biol. Chem. 264:11974-11980 (1989)).

Anti-TNFα treatment has been suggested to treat a variety of patients suffering from an inflammatory disease, such as Crohn's disease, ulcerative colitis, arthritis, rheumatoid arthritis. Vide for example U.S. Pat. No. 5,919,542. TNF-alpha inhibitor therapy results among other things in reduced recruitment of of neutrophils to the site of infection (reduced secretion of GM-CSF) and reduced functionality of neutrophils (inhibition of neutrophils adherance). Further, it has been reported that some of the patients treated with anti-TNFα treatment have developed severe infections, some even fatal infections.

SUMMARY OF THE INVENTION

A subpopulation of patients receiving TNF-α inhibitor treatment of inflammatory diseases as discussed above suffer from severe infections after onset of the TNF-α inhibitor treatment.

By the present invention MBL treatment and/or prophylaxis of the TNF-α inhibitor treatment induced infections is suggested.

Mannan-binding lectin (MBL), synonymous to mannose-binding lectin, mannan-binding protein or mannose-binding protein (MBP), belongs to a subgroup of C-type lectins, termed collecting, since these soluble proteins are composed of subunits presenting three CRDs attached to a collagenous stalk[2]. MBL interact with carbohydrates presented by a wide range of micro-organisms and accumulating evidence shows that it plays an important role in the innate immune defence[3]. When bound to carbohydrate MBL is able to activate the complement system.

The complement system may be activated via three different pathways: the classical pathway, the alternative pathway, and the newly described third pathway, the mannan-binding lectin (MBL) pathway which is initiated by the binding of MBL to carbohydrates presented by micro-organisms. The components of the alternative pathway and of the MBL pathway are parts of the innate immune defence, also termed the natural or the non-clonal, immune defence, while the classical pathway involves cooperation with antibodies of the specific immune defence[4].

The human MBL protein is composed of up to 18 identical 32 kDa polypeptide chains[27], each comprising a short N-terminal segment of 21 amino acids including three cysteine residues, followed by 7 repeats of the collagenous motif Gly-X-Y interrupted by a Gln residues followed by another 12 Gly-X-Y repeats. A small 34 residue 'neck-region' joins the C-terminal $Ca^{2+}$-dependent lectin domain of 93 amino acids with the collagenous part of the molecule[28].

The collagenous regions of the three polypeptide chains combine to form a subunit which is stabilised covalently by disulphide bridges. Individual subunits are joined by disulphide bridges as well as by non-covalently interactions[27].

The concentration of MBL in human serum is largely genetically determined, but reportedly increases up to three-fold during acute phase reactions[8]. Three mutations causing structural alterations and two mutations in the promotor region are associated with MBL deficiency[9]. MBL deficiency is associated with susceptibility to a variety of infections.

A wide range of oligosaccharides can bind to MBL. As the target sugars are not normally exposed on mammalian cell surfaces at high densities, MBL does not usually recognize self-determinants, but is particularly well suited to interactions with microbial cell surfaces presenting repetitive carbohydrate determinants. In vitro, yeast (*Candida albicans* and *Cryptococcus neoformans*), viruses (HIV-1, HIV-2, HSV-2, and various types of influenza A) and a number of bacteria have been shown to be recognized by MBL. In the case of some bacteria, the binding with MBL is impaired by the presence of a capsule[13]. However, even encapsulated bacteria (*Neisseria meningitidis*) can show strong binding of MBL[14].

Thus, the invention features the use of MBL, purified from natural sources or from material produced by recombinant technologies, or by any other suitable MBL-producing cell line, for the prophylaxis and/or treatment of infections associated with a therapeutical or medical treatment with TNF-α inhibitors. The MBL may be given before or after start of the medical treatment and for any duration of time deemed suitable.

By the term TNF-α inhibitors is meant any treatment having neutralizing and/or inhibiting activity against TNF-α. A TNF-α inhibitor may be a compound or a composition comprising anti-TNF-α antibodies, and/or anti-TNF-α peptides. Typically the TNF-α inhibitors bind to TNF-α blocking its interaction with cell surface TNF receptors thereby neutralizing and/or inhibiting the activity of TNF-α.

Also TNF-α inhibitors may be peptides or often compounds capable of binding to the TNF-α thereby inhibiting and/or neutralizing the biological activity of TNF-α. Examples of peptides are soluble TNF-α receptor complex or fragments thereof. Also, combinations of antibodies with TNF-α receptors or fragments thereof have been used as TNF-α inhibitors.

For example a chimeric monoclonal antibody comprised of human constant and murine variable regions, an example hereof is a drug "REMICADE" from Centocor, Inc., binding specifically to TNF-α.

Another example of a TNF-α inhibitor is dimeric fusion protein consisting of the extracellular ligand-biding portion of the human 75 kilodalton tumor necrosis factor receptor linked to the Fc portion of human IgG1. An example hereof is the drug "ENBREL" from ImmunexCorporation, wherein the Fc component of etnercept contains the $C_H2$ domain, the $C_H3$ domain and the hinge region, but not the $C_H1$ domain of IgG1.

Another example of TNF-α inhibitor therapy is the use of tolerance breaking vaccines, as those developed by M&E Biotech A/S (since 16 May, 2001 Pharmexa), capable of inducing autoantibodies directed against TNF-α.

MBL is believed to exert its antimicrobial activity mainly through its opsonizing activity (preparation of microorganisms for phagocytosis). This activity is dependent on activation of complement after binding of MBL to the microbial surface and deposition of C4b and C3b on the microorganism. MBL can also promote the direct complement-mediated killing of the microorganism through the activation of the terminal lytic pathway of complement and insertion of the membrane attack complex (MAC) in the membrane. This mechanism is considered of minor importance. Many microorganisms, such as Gram-positive bacteria, e.g., *Streptococcus pneumonia*, are resistant to MAC, but can be eliminated by opsonophagocytosis. Considering opsonophagocytosis as the main effector mechanism of MBL-mediated clearance of microorganisms, it is a surprise that MBL treatment could be of benefit to persons having an impaired phagocytic function due to TNF-α inhibitor therapy, in particular an impaired phagocytic function at a site of infection due to TNF-α inhibitor therapy.

It is possible according to the invention to prophylactically treat an infection in an individual receiving TNF-α inhibitor treatment. By prophylactically treating with MBL before or during the treatment it is possible to prevent a subsequent infection or to reduce the risk of the individual contracting an infection.

The invention is also directed to treatments of such deficiencies by infusion of MBL. Furthermore, the invention is directed to the use of MBL plasma concentrations for predicting the risk of infection of individuals undergoing therapy with TNF-α inhibitors.

In another aspect the present invention is related to the use of a composition comprising at least one mannan-binding lectin (MBL) subunit, or at least one oligomer comprising the at least one mannan-binding lectin (MBL) subunit, in the manufacture of a medicament for prophylactic, ameliorating or curative treatment of an infection in an individual initially having low plasma levels of MBL, such as plasma levels of about 0 mg/ml, or plasma levels in excess of 10 ng/. In particular the individual may be genetically disposed to an MBL deficiency or have acquired an MBL deficiency leading to an increased risk of suffering from infections. Accordingly, the invention also concerns treatment of infections in individuals suffering from a mannan-binding lectin (MBL) deficiency including any deficiency in the production of MBL and/or function of MBL, in particular however, individuals which furthermore receive treatment with a TNF-α inhibitor.

In yet another aspect there is provided a method for estimating the probability of the occurrence of any clinically significant infection in an individual undergoing therapy with TNF-α inhibitors, said method comprising the step of measuring the concentration of MBL in plasma or serum obtained from the individual, and estimating the probability on the basis of the measured concentration.

Also, by genotyping the individuals in question it is possible to estimate the probability of the occurrence of any clinically significant infection in an individual undergoing therapy with TNF-α inhibitors.

DETAILED DESCRIPTION OF THE INVENTION

TNF related pathologies include, but are not limited to, the following:

(A) acute and chronic immune and autoimmune pathologies, such as systemic lupus erythematosus (SLE) rheumatoid arthritis, thyroidosis, graft versus host disease, scleroderma, diabetes mellitus, Graves' disease, and the like;

(B) infections, including, but not limited to, sepsis syndrome, cachexia, circulatory collapse and shock resulting from acute or chronic bacterial infection, acute and chronic parasitic and/or infectious diseases, bacterial, viral or fungal, such as a HIV, AIDS (including symptoms of cachexia, autoimmune disorders, AIDS dementia complex and infections);

(C) inflammatory diseases, such as chronic inflammatory pathologies and vascular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology:

(D) neurodegenerative diseases, including, but are not limited to, demyelinating diseases, such as multiple sclerosis and acute transverse myelitis;

extrapyramidal and cerebellar disorders' such, as lesions of the corticospinal system;

disorders of the basal ganglia or cerebellar disorders;

hyperkinetic movement disorders such as Huntington's Chorea and senile chorea;

drug-induced movement disorders, such as those induced by drugs which block CNS dopamine receptors;

hypokinetic movement disorders, such as Parkinson's disease;

Progressive supranucleo palsy;

Cerebellar and Spinocerebellar Disorders, such as astructural lesions of the cerebellum;

spinocerebellar degenerations (spinal ataxia, Friedreich's ataxia, cerebellar cortical degenerations, multiple systems degenerations (Mencel, Dejerine-Thomas, Shi-Drager, and Machado-Joseph); and systemic disorders (Refsum's disease, abeta-lipoprotemia, ataxia, telangiectasia, and mitochondrial multi.system disorder);

demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, or any subset thereof;

(E) malignant pathologies involving TNF-secreting tumors or other malignancies involving TNF, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or *Mycosis fungoides*)); and (F) alcohol-induced hepatitis.

See, e.g., Berkow et al, eds., The Merck Manual, 16th edition, chapter 11, pp 1380-1529, Merck and Co., Rahway, N.J., 1992, which reference, and references cited therein, are entirely incorporated herein by reference.

Such treatment comprises parenterally administering a single or multiple doses of the antibody, fragment or derivative. Preferred for human pharmaceutical use are high affinity potent hTNF-α-inhibiting and/or neutralizing murine and chimeric antibodies, fragments and regions.

Anti-TNF peptides or MAbs can be administered by any means that enables the active agent to reach the agent's site of action in the body of a mammal. In the case of the antibodies of this invention, the primary focus is the ability to reach and bind with TNF released by monocytes and macrophages or other TNF producing cells. Because proteins are subject to being digested when administered orally, parenteral administration, i.e., intravenous, subcutaneous, intramuscular, would ordinarily be used to optimize absorption.

Infections related to TNF-α inhibitor treatment may be prevented and/or treated in individuals independent on their serum MBL level. In particular infections may be prevented when administering MBL to these individuals having an MBL level in excess of 10 ng/ml serum. Also, individuals having an MBL level in excess of 50 ng/ml serum may be in need of treatment, such as individuals having an MBL level in excess of 100 ng/ml serum, and individuals having an MBL level in excess of 150 ng/ml serum.

Also the MBL treatment of infections may be conducted by administering MBL to these individuals in combination with relevant antibiotics, anti-viral agents or anti-fungal agents.

In particular, individuals at risk of acquiring infection resulting from treatment with TNF-α inhibitors will benefit from being prophylactically treated with MBL before, during and maybe also after the treatment in order to prevent infections associated with or resulting from the anti TNF-α treatment.

Generally all individuals being treated with TNF-α inhibitors should be treated with MBL independent on their specific MBL level. The reason behind this is that infection may lead to MBL depletion, and therefore an MBL "booster", increasing the MBL level initially will reduce the risk of MBL depletion to a level below a deficiency level, and the immune defence of these patients can be reinforced by administration of recombinant or natural plasma-derived MBL. In particular infections may be prevented when administering MBL to individuals having an MBL level in excess of 10 ng/ml serum. Also, individuals having an MBL level in excess of 50 ng/ml serum may be in need of treatment, such as individuals having an MBL level in excess of 100 ng/ml serum, and individuals having an MBL level in excess of 150 ng/ml serum.

The present inventors have also shown herein that in particular individuals having an MBL level below 500 ng/ml serum will benefit from the MBL treatment. Consequently, in particular individuals having an MBL level below 400 ng/ml will benefit, such as individuals having an MBL level below 300 ng/ml, such as individuals having an MBL level below 250 ng/ml, such as individuals having an MBL level below 200 ng/ml.

Thus, in a preferred embodiment the present invention relates to the use of MBL for manufacturing of a medicament for treatment of individuals having an MBL level in serum in the range of 10-500 ng/ml, such as in the range of 50-500 ng/ml for treating and/or preventing infections.

One group of individuals being in need of MBL treatment in order to prevent and/or treat infections are individuals having a low level of functional MBL, independent on the level of MBL as such. This is due to the fact, that for some mutations of the MBL it has been found, that although MBL subunits and oligomers thereof are expressed in serum the functionality thereof are low. The functionality or functional activity of MBL may be estimated by its capacity to form an MBL/MASP complex leading to activation of the complement system. When C4 is cleaved by MBL/MASP an active thiol-ester is exposed and C4 becomes covalently attached to nearby nucleophilic groups. A substantial part of the C4b will thus become attached to the coated plastic well and may be detected by anti-C4 antibody.

A quantitative TRIFMA for MBL functional activity is constructed by 1) coating microtitre wells with 1 mg mannan in 100 ml buffer; 2) blocking with Tween-20; 3) applying test samples, e.g. diluted MBL preparations 4) applying MBL deficient serum (this leads to the formation of the MBL/MASP complex); alternatively the MBL and the MBL deficient serum may be mixed before application with the microtitre wells; 5) applying purified complement factor C4 at 5 mg/ml; 6) incubate for one hour at 37° C.; 7) applying Eu-labelled anti-C4 antibody; 8) applying enhancement solution; and 9) reading the Eu by time resolved fluorometry. Between each step the plate is incubated at room temperature and washed, except between step 8 and 9.

Estimation by ELISA may be carried out similarly, e.g. by applying biotin-labelled anti-C4 in step 7; 8) apply alkaline phosphatase-labelled avidin; 9) apply substrate; and 10) read the colour intensity.

The functionality may be expressed as the specific activity of MBL, such as 1 unit of MBL activity per ng MBL. A non-functional MBL may be defined as MBL having a specific activity less than 50% of plasma MBL specific activity, such as less than 25% of plasma MBL specific activity, wherein the plasma MBL is purified from an individual not suffering from any MBL mutations. In particular the reference plasma MBL is plasma pool LJ 6.57 Apr. 28, 1997.

Thus, the present invention also relates to the prevention and/or treatment of infection in individuals having a mutation in their MBL gene leading to a reduced expression of MBL and/or expression of non-functional MBL.

In particular such mutations in the MBL gene can lead to a change of aminoacid number 52 (numbering including the leader peptide of MBL) from arginine to cysteine, aminoacid number 54 from glycine to aspartic acid or amino acid number 75 from glycine to glutamic acid.

Also mutations in the promoter region of the MBL gene can lead to lowered levels of MBL. In particular mutations at position −221 have an influence on the expression of MBL.

The MBL sequence may be found in swiss.prot under accession No: 11226

The MBL composition used to manufacture an MBL medicament may be produced from any MBL source available. The MBL source may be natural MBL, whereby the MBLs are produced in a native host organism, meaning that MBL is produced by a cell normally expressing MBL. One usual method of producing an MBL composition is by extraction of MBL from human body liquids, such as serum or plasma, but MBL may also be harvested from cultures of hepatocytes.

In another aspect the MBL oligomers are produced by a host organism not natively expressing an MBL polypeptide, such as by recombinant technology.

In a first embodiment the MBL source may be serum, from which an MBL composition is obtained by purification from serum, plasma, milk product, colostrum or the like by a suitable purification method, such as affinity chromatography using carbohydrate-derivatised matrices, such as mannose or mannan coupled matrices. Such a method is discussed in WO99/64453, wherein the purification process is followed by a virus-removal step in order to remove infectious agents from the MBL source, since one of the major problems with proteins purified from body liquids is the risk of introducing infectious agents in combination with the desired protein. WO99/64453 is hereby incorporated by reference.

The MBL composition used to manufacture an MBL medicament preferably comprises MBL oligomers having a size distribution substantially identical to the size distribution of MBL in serum, such as a size distribution profile at least 50% identical to the size distribution profile of MBL in serum. By identical is meant that at least 50% of the oligomers has an apparent molecular weight higher than 200 kDa, when analysed by SDS-PAGE and/or Western blot.

In a more preferred embodiment the size distribution profile is at least 75% identical to the size distribution profile of MBL in serum, such as at least 90% identical to the size distribution profile of MBL in serum, and more preferred at least 95% identical to the size distribution profile of MBL in serum.

When purifying from an MBL source initially having another size distribution profile it is preferred that the affinity chromatography used to purify from the MBL source favours purification of oligomers having an apparent molecular weight higher than 200 kDa. This is obtained by using a carbohydrate-derivatized matrix having substantially no affinity to subunits and/or dimers of MBL. Preferably the carbohydrate-derivatized matrix has affinity for substantially only tetrameric, pentameric and/or hexameric recombinant MBLs.

The matrix may be derivatized with any carbohydrate or carbohydrate mixture whereto MBL binds and for which binding of the higher oligomers of MBL are favoured. The carbohydrate-derivatized matrix is preferably a hexose-derivatized matrix, such as a mannose- or a N-acetyl-glucosamin derivatized matrix, such as most preferably a mannose-derivatized matrix.

The selectivity of the carbohydrate-derivatized matrix is obtained b securing that the matrix as such, i.e. the un-derivatized matrix has substantially no affinity to MBL polypeptides, in particular no affinity to MBL trimers or smaller oligomers. This may be ensured when the matrix as such is carbohydrate-free. In particular the matrix should not contain any Sepharose or the like. It is preferred that the matrix consists of a non-carbohydrate containing polymer material, such as FRACTOGEL®TSK beads from Merck.

After application of the MBL source the column is washed, preferably by using non-denaturing buffers, having a composition, pH and ionic strength resulting in elimination of proteins, without eluting the higher oligomers of MBL.

Such as buffer may be TBS. Elution of MBL is performed with a selective desorbing agent, capable of efficient elution of highed oligomers of MBL, such as TBS comprising a desorbing agent, such as EDTA (for example 5 mM EDTA) or mannose (for example 50 mM mannose), and MBL oligomers are collected. Such a purification method is described in co-pending International patent application having the title "Recombinant Human Mannan Binding Lectin" filed the same day as the present application.

In a preferred aspect a clinical grade MBL composition is obtained by using an MBL source produced by recombinant technology, wherein the MBL source is the culture media from culturing of MBL producing cells.

Thus, the present invention encompasses MBL produced by a process of producing a recombinant mannan binding lectin (MBL), comprising the steps of:

preparing a gene expression construct comprising a DNA sequence encoding a MBL polypeptide or a functional equivalent thereof, transforming a host cell culture with the construct, cultivating the host cell culture, thereby obtaining expression and secretion of the polypeptide into the culture medium, followed by obtaining a culture medium comprising human recombinant MBLs.

The culture medium comprising the human recombinant MBL polypeptides may then be processed as described above for purification of MBL.

The MBL polypeptide is preferably a mammalian MBL polypeptide, such as more preferably a human MBL polypeptide. The gene expression construct may be produced by conventional methods known to the skilled person, such as described in U.S. Pat. No. 5,270,199.

In another embodiment the gene expression construct is prepared as described in PCT/DK00/00246.

The expression is preferably carried out in e.g. mammalian cells, the preparation according to the invention results from the use of an expression vector comprising intron sequence(s) from an MBL gene and at least one exon sequence. Regarding the transgenic animals as expression system this term is in this context animals which have been genetically modified to contain and express the human MBL gene or fragments or mimics hereof.

In addition to the purification method it is preferred that the gene expression construct and the host cell also favours production of higher oligomers, which has been found to be possible by using a gene expression construct comprising at least one intron sequence from the human MBL gene or a functional equivalent thereof. malian cells and cells from insects.

In particular the MBL composition is used for treatment and/or prophylaxis of an infection associated with TNF-α inhibitor treatment in an individual. Any microbiological infections may be treated and/or prevented with MBL, i.e. any infection caused by a microbial species.

Consequently, the MBL composition may be used for preventing and/or treating an infection in an individual wherein the microbial species is a fungus, a yeast, a protozoa, a parasite and/or a bacteria.

Also, the MBL composition may be used for treating infection, wherein the microbial species is resistent to usual medicaments, such as infections for which the bacterial species is resistent to at least one antibiotic medicament. More important is the prophylaxis and/or treatment of infections for which the bacterial species is multiresistent.

The individuals may suffer from infections caused by pathogenic bacterial species, such as *Streptococcus pneumonia,* Salmonella and Staphylococcal species.

It is however well-known that in particular immuno-compromised individuals also often suffer from infections caused by bacterial species, that are normally nonpathogenic, i.e. opportunistic pathogens, e.g. *E. coli* species, and many of these species are resistent to usual antibiotic treatment.

The infection associated with the condition may also be a viral infection, such as a viral infection wherein the virus is a retrovirus.

Also, the immuno-compromised condition may be an infection with the retrovirus Human Immunodeficiency Virus (HIV). However, the viral infections treated and/or prevented according to the invention are normally not caused by a retrovirus, but may for example be caused by a DNA virus.

Parasites according to the present invention may for example be selected from the group consisting of Malaria (*Plasmodium. falciparum, P. vivax, P. malariae*), Schistosomes, Trypanosomes, Leishmania, *Filarial nematodes,* Trichomoniasis, Sarcosporidiasis, Taenia (*T. saginata, T. solium*), Leishmania, *Toxoplasma gondii,* Trichinelosis (*Trichinella spiralis*) or Coccidiosis (Eimeria species).

The medicament may be produced by using the eluant obtained from the affinity chromatography as such. It is however preferred that the eluant is subjected to further purification steps before being used.

In addition to the MBL oligomers, the medicament may comprise a pharmaceutically acceptable carrier substance and/or vehicles. In particular, a stabilising agent may be added to stabilise the MBL proteins. The stabilising agent may be a sugar alcohol, saccharides, proteins and/or aminoacids. Examples of stabilising agents may be maltose or albumin.

Other conventional additives may be added to the medicament depending on administration form for example. In one embodiment the medicament is in a form suitable for injections. Conventional carrier substances, such as isotonic saline, may be used.

In another embodiment the medicament is in a form suitable for pulmonal administration, such as in the form of a powder for inhalation or creme or fluid for topical application.

The route of administration may be any suitable route, such as intravenously, intramusculary, subcutanously or intradermally. Also, pulmonal or topical administration is envisaged by the present invention.

The MBL composition may also be administered simultaneously, sequentially or separately with the TNF-α inhibitor treatment. The medicament may be administered for a period before the onset of administration of TNF-α-inhibitor and/or during at least a part of the TNF-α-inhibitor treatment.

The MBL composition is administered in suitable dosage regimes, in particularly it is administered repeatedly at suitable intervals, such as once or twice a week, starting before onset of TNF-α-inhibitor therapy and maintained at intervals, for example once a week, at least during a part of the therapy period, preferably during the whole therapy period.

Normally from 1-100 mg is administered per dosage, such as from 2-10 mg, mostly from 5-10 mg per dosage depending on the individual to be treated, for example about 0.1 mg/kg body weight is administered.

The use of an MBL composition for the manufacture of a medicament may also further comprise the manufacture of another medicament, such as an anti-fungal, anti-yeast, anti-bacterial and/or anti-viral medicament for obtaining a kit-of.parts.

The anti-viral medicament may be a medicament capable of virus attenuation and/or elimination.

The invention also relates to an aspect of using a measurement of the MBL level as a prognostic marker for the risk of the individual of acquiring an infection, and thereby an indicative of the need for treatment. In particular an MBL level below 500 ng/ml is a prognostic marker indicative for treatment with MBL, in particular in an individual that receives and/or will receive and/or have received treatment with a TNF-α inhibitor.

The prognostic marker may be in relation to any infection, but is especially relevant as a prognostic marker for septicaemia or pneumonia in individuals undergoing TNF-α inhibitor therapy.

Thus, the present invention also relates to a method of using an MBL composition for preventing and/or reducing infections in an individual, the method comprising the steps of:

i) determining serum levels of MBL in an individual,
ii) estimating the probability of the occurence of a significant clinical infection in the individual, and optionally, administering an MBL composition to the individual.

The MBL level is measured in serum or plasma, and may be determined by time resolved immunofluorescent assay (TRIFMA), ELISA, RIA or nephelometry.

Also the MBL levels may be inferred from analysis of genotypes of the MBL genes as discussed above in relation to mutations of MBL leading to a decreased MBL level.

EXAMPLE

MBL Serum Levels in Patients Treated with TNF-α Inhibitors

Patients are selected among individuals that have received treatment with either etanercept or infliximab. Patients presenting clinically significant infections (CSI, defined as bacteriaemia or pneumonia) are identified by retrospective computer search of the patient database.

Before entering treatment blood is drawn into evacuated glass tubes containing EDTA (final concentration about 10 mM). The plasma is aliquoted and kept at −80° C. until assay. Plasma samples are similarly obtained from healthy blood donors. The patients are free of infections at the time of blood sampling.

The concentration of MBL is determined by a time resolved immunofluorescent assay (TRIFMA). Microtitre wells (fluoroNunc, Nunc, Kamstrup, Denmark) are coated with antibody by incubation overnight at room temperature with 500 ng anti-human MBL antibody (Mab 131-1, Statens Serum Institut, Copenhagen, Denmark) in 100 µl PBS (0.14 M NaCl, 10 mM phosphate, pH 7.4). After wash with Tween-containing buffer (TBS, 0.14 M NaCl, 10 mM Tris/HCl, 7.5 mM NaN$_3$, pH 7.4 with 0.05% Tween 20) test samples (plasma 1/20) and calibrator dilutions are added in TBS/Tween with extra NaCl to 0.5 M and 10 mM EDTA.

After overnight incubation at 4° C. and wash, the developing europium-labelled antibody (12.5 ng Mab 131-1 labelled with the Eu-containing chelate, isothiocyanato-benzoyl-diethylene-triamine-tetra acetic acid, according to the manufacturer, Wallac, Turku, Finland) is added in TBS/Tween with 25 µM EDTA.

Following incubation for 2 h and wash, fluorescence enhancement solution is added (Wallac) and the plates are read on a time resolved fluorometre (Delfia 1232, Wallac). The calibration curve is made using dilutions of one plasma, which is kept alliquoted at −80° C.

Based on the above outlined method the MBL serum level of patients with CSI as compared to non-CSI patients is compared.

References

1. Weis W I, Taylor M E and Drickamer K (1998) The C-type lectin superfamily in the immune system. *Immunological Reviews* 163: 19-34
2. Holmskov, U., Malhotra, R., Sim, R. B., and Jensenius, J. C. (1994) Collectins: collagenous C-type lectins of the innate immune defense system. *Immunol. Today* 15:67-74.
3. Turner, M. W. (1996) Mannose-binding lectin: the pluripotent molecule of the innate immune system. *Immunol. Today* 17:532-540.
4 Janeway C A, Travers P, Walport M and Capra J D (1999) Immunobiology, the immune system in health and disease, Fourth Edition, Churchill Livingstone)
5. Matsushita, M. and Fujita, T (1992). Activation of the classical complement pathway by mannose-binding protein in association with a novel C1s-like serine protease. *J. Exp. Med.* 176:1497-1502.
6. Thiel S, Vorup-Jensen T, Stover C M, Schwaeble W, Laursen S B, Poulsen K, Willis A C, Eggleton P, Hansen S, Holmskov U, Reid K B and Jensenius J C (1997) A second serine protease associated with mannan-binding lectin that activates complement. *Nature*, 386(6624): 506-510
7. Stover C M, Thiel S, Thelen M, Lynch N J, Vorup-Jensen T, Jensenius J C and Schwaeble W J (1999) Two constituents of the initiation complex of the mannan-binding lectin activation pathway of complement are encoded by a single structure gene. *J Immunol* 162: 3481-3490
8. Thiel S, Holmskov U, Hviid L, Laursen S B and Jensenius J C (1992) The concentration of the C-type lectin, mannan-binding protein, in human plasma increases during an acute phase response. *Clin Exp Immunol* 90: 31-35
9. Madsen, H. O., Garred, P., Kurtzhals, J. A., Lamm, L. U., Ryder, L. P., Thiel, S., and Svejgaard, A. (1994) A new frequent allele is the missing link in the structural polymorphism of the human mannan-binding protein. *Immunogenetics* 40:37-44.
10. Summerfield J A, Ryder S, Sumiya M, Thursz M, Gorchein A, Monteil M A and Turner M W (1995) Mannose binding protein gene mutations associated with unusual and severe infections in adults. *Lancet* 345: 886-889
11. Garred P, Madsen H O, Hofmann B and Svejgaard A (1995) Increased frequency of homozygosity of abnormal mannan binding protein alleles in patients with suspected immunodeficiency. *Lancet* 346: 941-943
12. Summerfield J A, Sumiya M, Levin M and Turner M W (1997) Association of mutations in mannose-binding protein gene with childhood infection in consecutive hospital series. *BioMed J* 314: 1229-1232
13. van Emmerik, L C, Kuijper, E J, Fijen, C A P, Dankert, J, and Thiel, S (1994) Binding of mannan-binding protein to various bacterial pathogens of meningitis. *Clin. Exp. Immunol.* 97:411-416.

14. Jack D L, Dodds A W, Anwar N, Ison C A, Law A, Frosch M, Turner M W and Klein N J (1998) Activation of complement by Mannose-binding lectin on isogenic mutants of *Neisseria meningitidis* seroproup B. *J Immunol* 160: 1346-1353
15. Miller, M. E., Seals, J., Kaye, R., and Levitsky, L. C. (1968) A familial, plasma-associated defect of phagocytosis. A new case of recurrent bacterial infections. *The. Lancet:*60-63.
16. Super, M., Thiel, S., Lu, J., Levinsky, R. J., and Turner, M. W. (1989) Association of low levels of mannan-binding protein with a common defect of opsonisation. *Lancet* 2:1236-1239.
17. Nielsen, S. L., Andersen, P. L., Koch, C., Jensenius, J. C., and Thiel, S. (1995) The level of the serum opsonin, mannan-binding protein in HIV-1 antibody-positive patients. *Clin. Exp. Immunol.* 100:219-222.
18. Christiansen, O. B., Kilpatrick, D. C., Souter, V., Varming, K., Thiel, S., Jensenius, J. C. (1999) Mannan-binding lectin deficiency is associated with unexplained recurrent miscarriage. *Scand. J. Immunol.,* 49, 193-196
19. Garred, P, Harboe, M, Oettinger, T, Koch, C, and Svejgaard, A (1994) Dual role of mannan-binding protein in infections: Another case of heterosis? *Eur. J. Immunogen.* 21:125-131.
20. Hoal-Van Helden E G, Epstein J, Victor T C, Hon D, Lewis L A, Beyers N, Zurakowski D, Ezekowitz A B, Van Helden P D (1999) Mannose-binding protein B allele confers protection against tuberculous meningitis. *Pediatr Res* 45:459-64
21. Fischer, P B, Ellerman-Eriksen, S, Thiel, S, Jensenius, J C, and Mogensen, S C (1994) Mannan-binding protein and conglutinin mediate enhancement of herpes simplex virus type-2 infection in mice. *Scand J Immunol* 39:439-445.
22. Valdimarsson H, Stefansson M, Vikingsdottir T, Arason G J, Koch C, Thiel S and Jensenius J C (1998) Reconstitution of opsonizing activity by infusion of mannan-binding lectin (MBL) to
24. Pizzo, P A (1993), Management of fever in patients with cancer and treatment-induced neutropenia, *N Eng J Med,* 328, 1323-1332.
25. Aittoniemi, J., Miettinen, A., Laine, S., Sinisalo, M., Laippala, P., Vilpo, L, Vilpo, J. (1999), Opsonising immunoglobulins and mannan-binding lectin in chronic lymphocytic leukemia, *Leuk Lymphoma* July; 34(34):3815
26. Lehrnbecher T, Venzon D, de Haas M, Chanock S J, Kuhl J. (1999) Assessment of measuring circulating levels of interleukin6, interleukin8, Creactive protein, soluble Fc gamma receptor type III, and mannosebinding protein in febrile children with cancer and neutropenia. Clin Infect Dis, August; 29(2):4149.
27. Lu, J., Thiel, S., Wiedemann, H., Timpl, R. & K. B. M. Reid (1990) Binding of the pentamer/hexamer forms of mannan-binding protein to zymosan activates the proenzyme $C1r_2C1s_2$ complex, of the classical pathway of complement without involvement of C1q. *J. Immunol.* 144:2287-2294.
28. Sastry, K., Herman, G. A., Day, L., Deignan, E., Bruns, G., Morton, C. C. & R. A. B. Ezekowitz (1989) The human mannose-binding protein gene. *J. Exp. Med.* 170: 1175-1189.
29. Lipscombe, R. J., Sumiya, M., Summerfield, J. A. & M. W. Turner (1995) Distinct physicochemical characteristics of human mannose-binding protein expressed by individuals of differing genotype. *Immunology* 85:660-667.

The invention claimed is:

1. A method of treating or reducing the risk of an infection in an individual at increased risk of infection, due to impaired phagocytic function, as a result of treatment with a TNF-α inhibitor which inhibitor treatment by itself results in acute suppression of macrophage action leading to reduced recruitment and functionality of macrophages and neutrophils, the method comprising:
   administering an effective amount of a human mannan-binding lectin (MBL) composition, to an individual who has received or is receiving a medical treatment with a TNF-α inhibitor, said treatment resulting in impaired phagocytic function, whereby infection is treated or the risk of infection is reduced.

2. The method of claim 1, wherein the MBL composition comprises at least one mannan-binding lectin (MBL) oligomer comprising the at least one mannan-binding lectin (MBL) subunit.

3. The method of claim 2, wherein said oligomer is selected from the group of oligomers consisting of tetramers, pentamers and/or hexamers.

4. The method of claim 1, wherein the infection is an infection caused by a microbial species.

5. The method of claim 4, wherein the microbial species is a fungus.

6. The method of claim 4, wherein the microbial species is a yeast.

7. The method of claim 4, wherein the microbial species is a bacterium.

8. The method of claim 7, wherein the bacterial species is resistant to at least one antibiotic medicament.

9. The method of claim 7, wherein the bacterial species is multiresistant.

10. The method of claim 7, wherein the bacterial species is pathogenic.

11. The method of claim 1 wherein serum MBL levels are determined prior to said administration.

12. The method of claim 11, wherein serum levels of MBL in the individual are determined by quantitative analysis.

13. The method of claim 12, wherein the analysis comprises at least one of enzyme-linked immunosorbent assay (ELISA), time-resolved immunofluorimetric assay (TRIFMA), radioimmunoassay (RIA) or nephelometry.

14. The method of claim 1 in which said TNF-α inhibitor is capable of reducing MBL levels in said individual.

15. The method of claim 1 wherein said MBL composition comprises a 96 kDa MBL subunit as a separate monomeric molecule rather than as a moiety of an MBL oligomer.

16. The method of claim 1 wherein phagocytic function is determined prior to said administration.

17. The method of claim 1, wherein the individual has, prior to administration, serum levels of MBL below 500 ng/ml.

18. The method of claim 1, wherein the individual has, prior to administration, serum levels of MBL below 400 ng/ml.

19. The method of claim 1, wherein the individual has, prior to administration, serum levels of MBL below 300 ng/ml.

20. The method of claim 1, wherein the individual has, prior to administration, serum levels of MBL below 250 ng/ml.

21. The method of claim 1, wherein the individual has, prior to administration, serum levels of MBL below 200 ng/ml.

22. A method of treating a disease which is a TNF-related pathology, which disease is responsive to treatment with a TNF-α inhibitor, while mitigating the increased risk of infection attributable, due to impaired phagocytic function, to said treatment with a TNF-α inhibitor, which inhibitor treatment by itself results in acute suppression of macrophage action, leading to reduced recruitment of macrophages and neutrophils, comprising administering, to an individual, (1) an effective amount of TNF-α inhibitor in pharmaceutical form, or an effective amount of a substance which elicits production in said individual of an effective amount of a TNF-α inhibitor, where said inhibitor, if administered alone, would result in impaired phagocytic function, and (2) an effective amount of a human mannanbinding lectin (MBL) composition, to said individual, thereby treating said disease while treating an infection, or mitigating the increased risk of infection, attributable to such treatment in said individual.

23. The method of claim 22, wherein the composition is administered to the individual prior to said TNF-alpha inhibitor treatment.

24. The method of claim 22 wherein the administration of (1) is of a TNF-α inhibitor in pharmaceutical form.

25. The method according to claim 24, wherein the administration (1) is of a TNF-α inhibitor which is an antibody directed against TNF-α.

26. The method according to claim 24, wherein the administration (1) is of a TNF-α inhibitor which is a fusion protein comprising portions of TNF-α receptor.

27. The method according to claim 24, wherein the TNF-α inhibitor is selected from etanercept and infliximab.

28. The method of claim 24, wherein the individual has, prior to administration (2), a serum level of MBL in excess of 10 ng/ml.

29. The method of claim 28, wherein the serum MBL level is the functional serum MBL level.

30. The method of claim 28, wherein the individual has, prior to administration (2), MBL serum levels below 500 ng/ml.

31. The method of claim 30, wherein the individual has, prior to administration (2), serum levels of MBL in excess of 75 ng/ml.

32. The method of claim 30, wherein the individual has, prior to administration (2), serum levels of MBL in excess of 100 ng/ml.

33. The method of claim 30, wherein the individual has, prior to administration (2), serum levels of MBL in excess of 150 np/ml.

34. The method of claim 24, wherein the individual has, prior to administration (2), a serum level of MBL in excess of 50 ng/ml.

35. The method of claim 34, wherein the serum MBL level is the functional serum MBL level.

36. The method of claim 24, wherein the individual has, prior to administration (2), serum levels of MBL in excess of 75 np/ml.

37. The method of claim 36, wherein the individual has, prior to administration (2), serum levels of MBL below 400 ng/ml.

38. The method of claim 36, wherein the individual has, prior to administration (2), serum levels of MBL below 300 ng/ml.

39. The method of claim 24, wherein the individual has, prior to administration (2), serum levels of MBL in excess of 100 np/ml.

40. The method of claim 24, wherein the individual has, prior to administration (2), serum levels of MBL in excess of 150 np/ml.

41. The method of claim 24, wherein the individual has, prior to administration (2), serum levels of MBL below 500 ng/ml.

42. The method of claim 24, wherein the individual has, prior to administration (2), serum levels of MBL below 400 ng/ml.

43. The method of claim 24, wherein the individual has, prior to administration (2), serum levels of MBL below 300 ng/ml.

44. The method of claim 24 in which the MBL composition and the TNF-α inhibitor are administered simultaneously.

45. The method of claim 44 in which the MBL composition and the TNF-α inhibitor are administered separately.

46. The method of claim 24 in which the MBL composition and the TNF-α inhibitor are administered sequentially.

47. The method of claim 24 in which said individual, after said TNF-α inhibitor treatment and prior to treatment with said MBL composition, has MBL levels which are significantly below normal.

48. The method of claim 24, further comprising administration of an effective amount of an antimicrobial medicament, other than an MBL composition, to which said infection is responsive.

49. The method of claim 24 wherein serum or plasma MBL levels are determined prior to said administration (2) and after said administration (1).

50. The method of claim 24 wherein phagocytic function is determined prior to said administration.

51. The method of claim 24, wherein the individual has, prior to administration (2), serum levels of MBL below 250 ng/ml.

52. The method of claim 24, wherein the individual has, prior to administration (2), serum levels of MBL below 200 ng/ml.

* * * * *